US009656228B2

(12) United States Patent
Palmer et al.

(10) Patent No.: US 9,656,228 B2
(45) Date of Patent: May 23, 2017

(54) DEVICE AND METHOD FOR MAKING SOLID BEADS

(75) Inventors: Daniel Palmer, Cardiff (GB); Richard Calder, Cardiff (GB); Owen Shadick, Cardiff (GB)

(73) Assignee: Midatech Pharma (Wales) Limited, Cardiff (GB)

( * ) Notice: Subject to any disclaimer, the term of this patent is extended or adjusted under 35 U.S.C. 154(b) by 428 days.

(21) Appl. No.: 12/999,578

(22) PCT Filed: Jun. 16, 2009

(86) PCT No.: PCT/GB2009/001492
§ 371 (c)(1),
(2), (4) Date: Feb. 15, 2011

(87) PCT Pub. No.: WO2010/004253
PCT Pub. Date: Jan. 14, 2010

(65) Prior Publication Data
US 2011/0160134 A1    Jun. 30, 2011

(30) Foreign Application Priority Data

Jun. 16, 2008 (GB) .................................. 0810990.2
Jan. 8, 2009 (GB) .................................. 0900264.3

(51) Int. Cl.
*A61K 9/50* (2006.01)
*B01J 2/08* (2006.01)
*A61K 9/16* (2006.01)

(52) U.S. Cl.
CPC .............. *B01J 2/08* (2013.01); *A61K 9/1647* (2013.01); *A61K 9/1694* (2013.01)

(58) Field of Classification Search
CPC ....... A61K 9/16; A61K 9/1611; A61K 9/1682
USPC .................................................. 424/464–485
See application file for complete search history.

(56) References Cited

U.S. PATENT DOCUMENTS

| 5,912,015 | A | 6/1999 | Bernstein et al. |
| 6,143,211 | A | 11/2000 | Mathiowitz et al. |
| 6,159,490 | A | 12/2000 | Deghenghi |
| 7,147,806 | B2 | 12/2006 | Castor |
| 7,223,440 | B2 | 5/2007 | Rickey et al. |
| 2003/0082236 | A1 | 5/2003 | Mathiowitz et al. |
| 2004/0009226 | A1 | 1/2004 | McHugh et al. |
| 2004/0071781 | A1 | 4/2004 | Chattopadhyay et al. |
| 2004/0220081 | A1 | 11/2004 | Kreitz et al. |
| 2005/0042294 | A1 | 2/2005 | Thanoo et al. |
| 2005/0069898 | A1* | 3/2005 | Moon ............. C12N 9/1252 435/6.16 |
| 2006/0003439 | A1* | 1/2006 | Ismagilov ............ B01F 5/0471 435/287.2 |
| 2006/0033224 | A1 | 2/2006 | Castor |
| 2006/0078888 | A1* | 4/2006 | Griffiths ............... B01F 3/0807 435/6.11 |
| 2006/0088595 | A1* | 4/2006 | Asakawa ............. A61K 9/0019 424/468 |
| 2006/0099271 | A1 | 5/2006 | Rickey et al. |
| 2006/0163385 | A1* | 7/2006 | Link .................... B01F 5/0682 239/424 |
| 2007/0042040 | A1 | 2/2007 | Porchet et al. |
| 2007/0196416 | A1 | 8/2007 | Li et al. |

FOREIGN PATENT DOCUMENTS

| CA | 2 189 254 C | 11/1995 |
| EP | 1 358 931 A | 11/2003 |
| JP | 2006-212570 A | 8/2006 |
| WO | WO 95/29664 A | 11/1995 |
| WO | 1999-515016 | 12/1999 |
| WO | WO 01/64332 A | 9/2001 |
| WO | WO 01/81566 A | 11/2001 |
| WO | WO 03/026733 A | 4/2003 |
| WO | 2006-522146 | 9/2006 |
| WO | WO 2007/072002 A | 6/2007 |
| WO | WO 2008/040959 A | 4/2008 |
| WO | WO 2008040959 A2 * | 4/2008 ................ B01J 2/06 |
| WO | 2010-505391 | 2/2010 |

OTHER PUBLICATIONS

Wessel, Hans Peter et al.: "Oligosaccharide Mimetics", *Glyoscience*, 2008, pp. 2079-2112.
Holgado, M.A. et al.: "Synthesis of lidocaine-loaded PLGA microparticles by flow focusing Effects on drug loading and release properties", *International Journal of Pharmaceutics*, 358 (2008), pp. 27-35.
Tan, Wei-Heong et al.: "Monodisperse Alginate Hydrogel Microbeads for Cell Encapsulation", *Adv. Mater.*, 2007, 19, pp. 2696-2701.
Taluja, Ajay et al.: "Novel approaches in microparticulate PLGA delivery systems encapsulating proteins", *J. Mater. Chem.*, 2007, 17, pp. 4002-4014.
Sah, Hongkee: "Microencapsulation techniques using ethyl acetate as a dispersed solvent: effects of its extraction rate on the characteristics of PLGA microspheres", *Journal of Controlled Release*, 47 (1997), pp. 233-245.

(Continued)

*Primary Examiner* — Micah-Paul Young
(74) *Attorney, Agent, or Firm* — Haug Partners LLP

(57) ABSTRACT

A method of making solid beads is disclosed, said method comprising: (i) providing a microfluidic device comprising a carrier fluid conduit and a functional fluid conduit which meet at a junction region; (ii) providing a laminar flow of a functional fluid comprising a solvent and a solute along the functional fluid conduit and providing a laminar flow of a carrier fluid along the carrier fluid conduit so as to form droplets of functional fluid in a flow of carrier fluid; (iii) cooling the segments of functional fluid in a conduit of the microfluidic device to form cooled (preferably frozen) droplets; and (iv) providing a liquid into intimate admixture with the cooled droplets so as to cause said solvent to exit said cooled droplets, thus forming solid beads. A microfluidic device for use in such a method is also disclosed.

18 Claims, 8 Drawing Sheets

(56) References Cited

OTHER PUBLICATIONS

Figure 1:
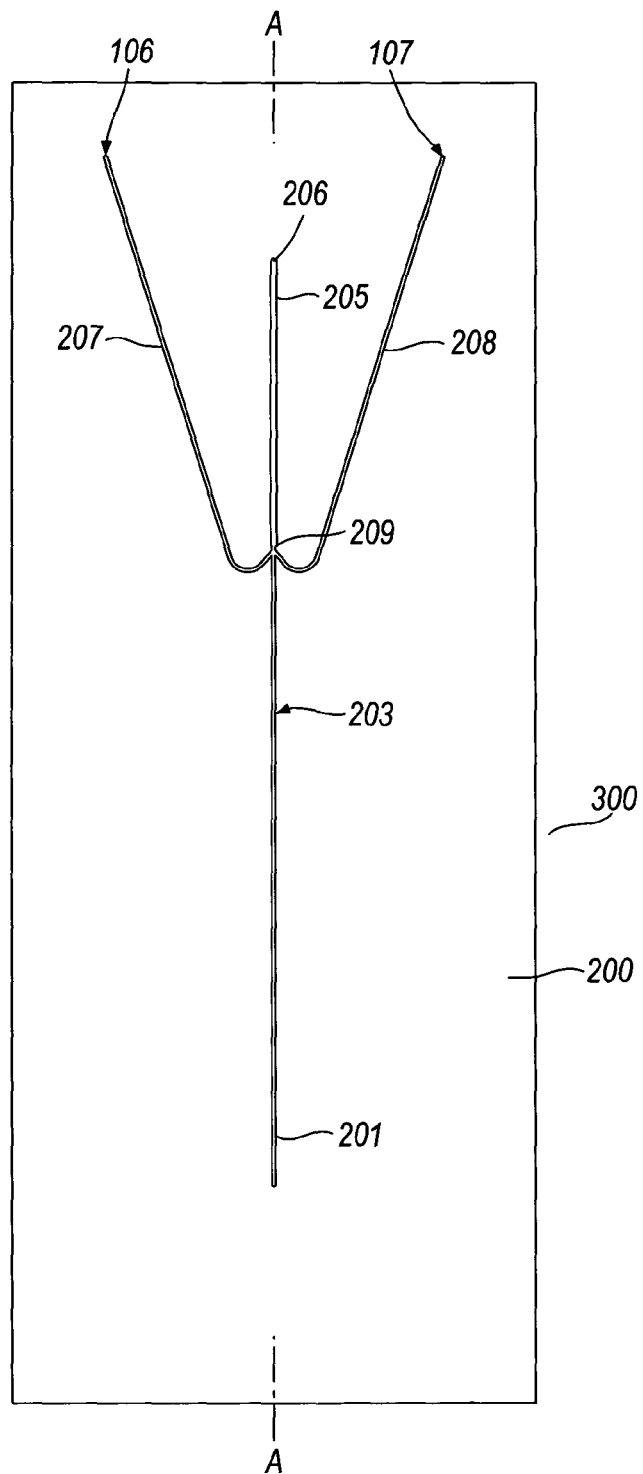

Chang, Jia-Yaw et al.: "Microfluidic assisted preparation of CdSe/ZnS nanocrystals encapsulated into poly(DL-lactide-*co*-glycolide) microcapsules", *Nanotechnology*, 18 (2007), pp. 1-8.

Freitas, Sergio et al.: "Flow-through ultrasonic emulsification combined with static micromixing for aseptic production of microspheres by solvent extraction", *European Journal of Pharmaceutics and Biopharmaceutics*, 61 (2005), pp. 181-187.

Freitas, Sergio et al.: "Microencapsulation by solvent extraction/evaporation: reviewing the state of the art of microsphere preparation process technology", *Journal of Controlled Release*, 102 (2005), pp. 313-332.

\* cited by examiner

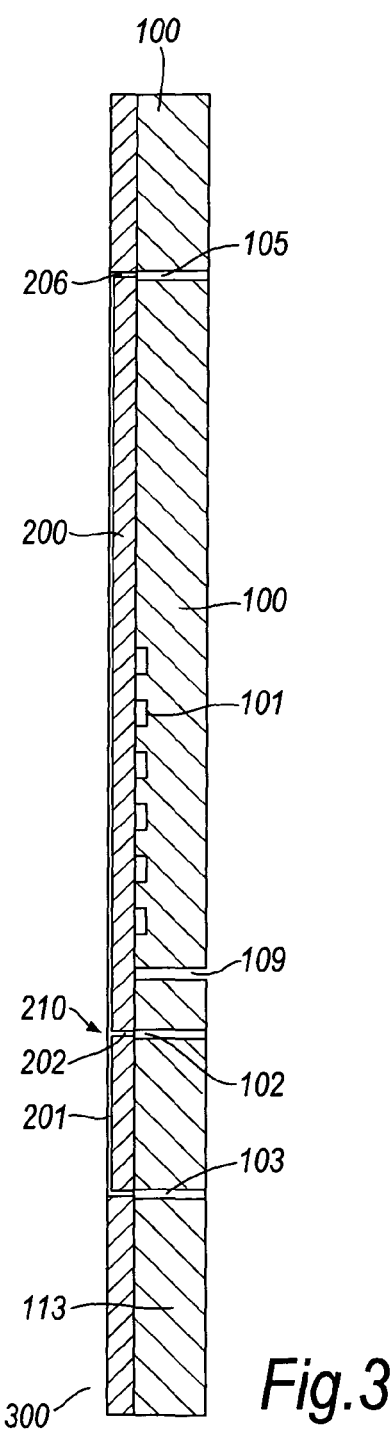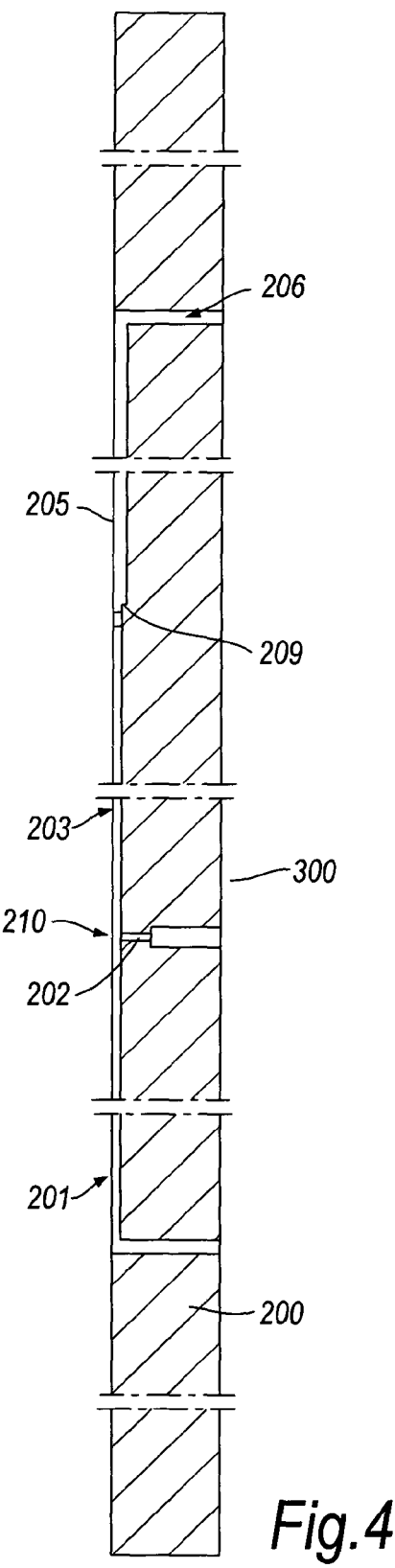
Fig.3
Fig.4

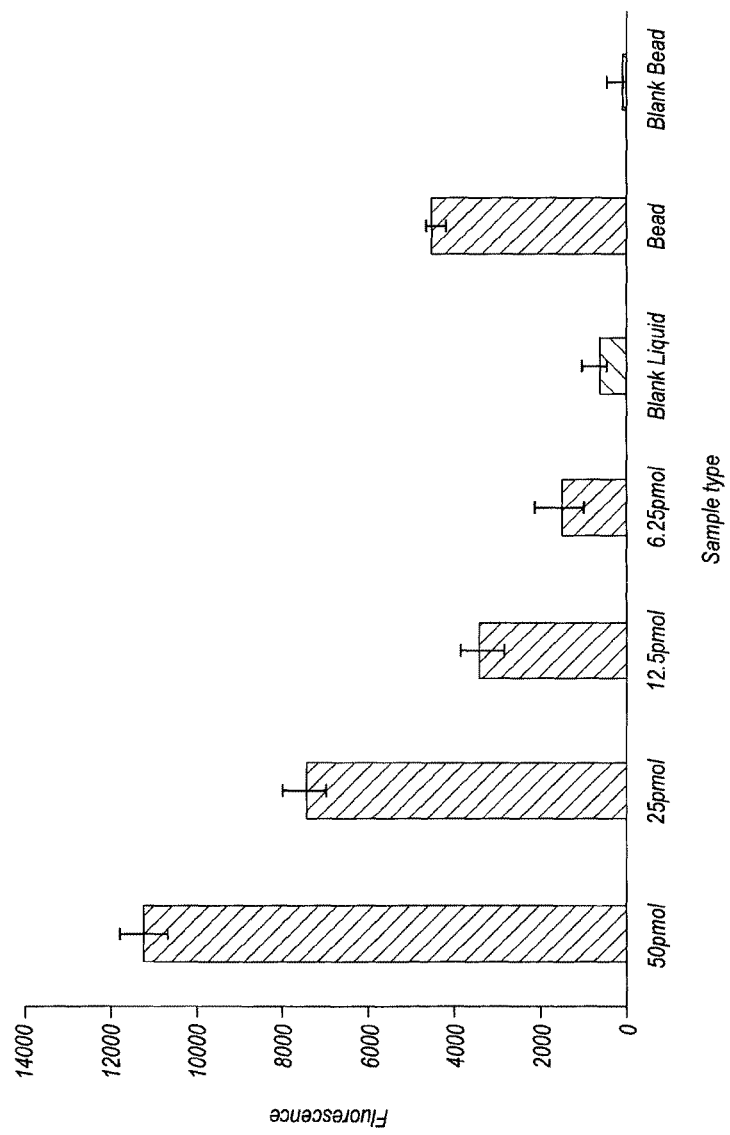

DEVICE AND METHOD FOR MAKING SOLID BEADS

This application is a 371 of PCT/GB2009/001492 filed on Jun. 16, 2009, published on Jan. 14, 2010 under publication number WO 2010/004253 A which claims priority benefits from British Patent Application Number 0810990.2 filed Jun. 16, 2008 and British Patent Application Number 0900264.3 filed Jan. 8, 2009, the disclosures of which are both incorporated herein by reference.

The present invention relates to a microfluidic device for the manufacture of solid beads (typically, but not exclusively, polymer beads containing some form of pharmaceutically active agent) and a method of making such beads.

Many methods are known for the manufacture of small, polymeric beads containing some form of pharmaceutically active agent. Such beads are used, especially but not exclusively, for the controlled release parenteral delivery of the active agent within the human or animal body. Illustrative therapeutic areas in which controlled release parenteral delivery may be particularly applicable include, for example, fertility treatment, hormone therapy, protein therapy, infection treatments (antibiotics and antifungals), cancer therapy, post-operative pain treatment, chronic pain treatment, vaccination/immunization, treatment of disorders of the central nervous system, and immunosuppression. The advantages of controlled release parenteral delivery in those and other therapeutic areas are well-documented and may include, for example, one or more of the following: improvement of the therapeutic response; improved safety (since, as compared with conventional parenteral dosage forms, less drug is required and the drug may be targeted to the in vivo site, avoiding high systemic levels); and improved patient compliance (through the possibility of lower dosing frequency and simpler dosage regimes). Typically, polymer beads can be used to effect controlled release of a therapeutic agent over periods of months.

Most methods for the manufacture of polymeric beads for therapeutics use solutions or mixtures of polymer and active agent to make liquid droplets from which solid beads are then made. Several techniques may be used to generate the liquid droplets, such as stirring of the solution/mixture or static mixing. These techniques generate beads with a broad distribution of bead sizes. Alternative techniques include dripping and spray formation which may also lead to the production of beads with a broad distribution of bead sizes. The liquid droplets generated by such methods may then be treated to remove the solvent. This is typically achieved by admixture of the droplets with large amounts of anti-solvent or by evaporation. This may lead to relatively large amounts of residual solvent in the solid beads and may also lead to the generation of beads with a broad distribution of bead sizes.

The present invention is addressed at solving one or more of the above-mentioned problems.

In accordance with a first aspect of the present invention, there is provided a microfluidic device comprising:

a carrier fluid conduit for the delivery of a carrier fluid;

a functional fluid conduit for the delivery of a functional fluid which is immiscible with the carrier fluid, the functional fluid conduit meeting the carrier fluid conduit at a junction region so that, in use, a flow of droplets of functional fluid in carrier fluid is formed at or downstream of the junction region;

a cooling conduit arranged for receiving the segmented flow from the junction region;

a cooler operable to cool fluid in the cooling conduit; and a desolvating conduit arranged for receiving fluid from the cooling conduit, the device being provided with an anti-solvent inlet for introducing an anti-solvent into the desolvating conduit.

The device of the present invention facilitates the manufacture of solid beads having beneficial size distribution characteristics and no more than a small amount of solvent remaining in the solid bead. The functional fluid typically comprises a solution comprising a solvent and a solute, the solute typically comprising a polymer. The components of the functional fluid are preferably so chosen that the droplets of functional fluid solidify when cooled in the cooling conduit to form solid droplets. The droplets may, for example, be frozen or in the form of a gel. A gel is defined herein as a substance which acts as a solid in the device of the present invention (i.e. deforms elastically and recovers and does not flow as a liquid would flow). In some circumstances, the droplets of functional fluid when cooled in the cooling conduit may not form a solid, but rather may be a liquid, typically of a high viscosity.

The components of the functional fluid may be premixed, but may instead be combined within the substrate, for example by means of two converging conduits. The polymer typically has a low solubility in the anti-solvent, whilst the solvent is miscible with the anti-solvent. The addition of the anti-solvent typically causes the solvent to pass out of the droplets, thus producing a solid bead.

The device may comprise a plurality of carrier fluid conduit for the delivery of a carrier fluid, the functional fluid conduit meeting the carrier fluid conduits at a junction region so that, in use, a flow of droplets of functional fluid in carrier fluid is formed at or downstream of the junction region.

The conduits mentioned above need not be discretely-identifiable conduits. For example, the cooling conduit and carrier fluid conduit may be merged into one another.

The cooler may comprise a cooling body comprising a thermally conductive material (such as a metal, for example, 316 stainless steel or aluminium). The cooling body is typically cooled when the cooler is operated. The cooling of the cooling body may be used to cool the cooling conduit by thermal conduction. The cooling body may be provided with a chilling channel for the carriage of a chilling fluid. The passage of a chilling fluid (typically a cold liquid) through the chilling channel causes the cooling body to cool. The chilling fluid preferably has a melting point of lower than −50° C. The chilling fluid is typically cooled externally of the device. The chilling fluid may be cooled by any suitable refrigeration device, for example a Julabo refrigerated circulator.

The cooling body of the cooler may further be provided with a heater. Such a heater may be used to heat the body; this may be useful in thawing any frozen liquids which may block any of the conduits of the device and for controlling the temperature of the anti-solvent and of the desolvation process.

A cooling body need not be provided. For example, the cooling conduit may be provided in a substrate of the microfluidic device, wherein the substrate is provided with a chilling channel for the carriage of a chilling fluid, the cooling conduit being in thermal communication with the chilling channel so that fluid in the cooling conduit may be cooled by chilling fluid in the chilling channel.

The device may be provided with a second thermally conductive body, the second thermally conductive body being associated with the carrier fluid conduit and the functional fluid conduit. The second thermally conductive body may be provided with a heater and/or cooler operable to regulate the temperature of liquids in the carrier fluid conduit and functional fluid conduit.

A thermally insulating gap may be provided between the body of the cooler and the second thermally conductive body. The thermally insulating gap may comprise a thermally insulating material, such as air. The gap helps inhibit cooling of the carrier fluid conduit and functional fluid conduit when the cooler is used to cool the cooling conduit.

The second thermally conductive body may be provided with a carrier fluid inlet for providing fluid to the carrier fluid conduit. The second thermally conductive body may be provided with a functional fluid inlet for providing fluid to the functional fluid conduit.

It is preferred that the device comprises one or more anti-solvent delivery conduits for delivering anti-solvent to the desolvating conduit via the anti-solvent inlet.

It is preferred that the cooling conduit arranged for receiving the segmented flow from the junction region is provided in a substrate (for example, by removing material from a substrate by milling or by laser action).

It is preferred that one or more of the carrier fluid conduit, the functional fluid conduit, the desolvating conduit and the anti-solvent delivery conduit(s) are provided in a substrate.

It is further preferred that the substrate is in thermal contact with a cooling part of the cooler. If the cooler comprises a body of thermally conductive material, it is preferred that the substrate is in intimate contact with the body of thermally conductive material.

If the cooler comprises a body of thermally conductive material, the body may be provided with one or more fluid inlets for delivering fluid to the anti-solvent delivery conduit (if present).

The term "microfluidic" is generally well-understood by those skilled in the art. The conduits in such microfluidic devices typically have widths of less than 2 mm, preferably less than 1 mm and more preferably from 0.1 to 0.5 mm. The depths of the conduits are typically less than 2 mm, preferably less than 1 mm and more preferably from 0.1 mm to 0.5 mm.

The flow rates of the fluids through the various conduits will depend, inter alia, on the cross-sectional area of the conduits. The flow rate, for example, of the functional fluid through the functional fluid conduit may typically be from about 0.01 to 0.2 ml/hour, especially 0.05 to 0.2 ml/hour (if the conduit has a cross-section of about 0.05 mm×0.15 mm). The flow rate, for example, of the functional fluid through the functional fluid conduit may typically be from about 1 to 20 ml/hour, (if the conduit has a cross-section of about 2 mm×2 mm). Such flow rates may be used when wanting to make larger particles, such as those which may be used in assays. The flow rate of the carrier fluid may typically be from about 1 to 4 ml/hour, especially 2 to 3 ml/hour (if the conduit has a cross-section of about 0.3 mm×0.3 mm). The flow rate of the carrier fluid may typically be from about 5 to 30 ml/hour (if the conduit has a cross-section of about 2 mm×2 mm). Such flow rates may be used when wanting to make larger particles, such as those which may be used in assays. The flow rate of the anti-solvent may typically be from about 0.25 to 3 ml/hour, especially 0.5 to 2 ml/hour (if the conduit has a cross-section of about 0.3 mm×0.3 mm). The flow rate of the anti-solvent is preferably so selected that, in the desolvating conduit, the volume of anti-solvent is lower than the volume of carrier fluid whilst being sufficient to ensure that there is a high probability of contact between the cooled droplets of functional fluid and the carrier fluid/anti-solvent interface. By way of illustration the flow rates may in some embodiments be such that the volume of carrier fluid is from 1 to 4 times the volume of anti-solvent. The flow rate of the anti-solvent may typically be from about 10 to 20 ml/hour (if the conduit has a cross-section of between 1 mm×1 mm and 2 mm×2 mm). Such flow rates may be used when wanting to make larger particles, such as those which may be used in assays.

It is preferred that the desolvating conduit has a larger cross-section than the cooling conduit. This may be achieved by providing a widening, for example a stepwise widening, in the desolvating conduit. A relatively large cross-section desolvating conduit causes the speed of flow of cooled droplets/forming beads through the desolvating conduit to be slower than the flow of the droplets through the cooling conduit. This may be beneficial if the anti-solvent chosen works relatively slowly which may be desirable to retain beads of more uniform size.

In accordance with a second aspect of the present invention, there is provided a method of making solid beads, said method comprising:
(i) providing a microfluidic device comprising a carrier fluid conduit and a functional fluid conduit which meet at a junction region;
(ii) providing a laminar flow of a functional fluid comprising a solvent and a solute along the functional fluid conduit and providing a laminar flow of a carrier fluid along the carrier fluid conduit so as to form droplets of functional fluid in a flow of carrier fluid;
(iii) cooling the droplets of functional fluid in a conduit of the microfluidic device to form cooled droplets; and
(iv) bringing a fluid into intimate admixture with the cooled droplets so as to cause said solvent to exit said cooled droplets, thus forming solid beads.

The cooled droplets formed in step (iii) typically have sufficient structural integrity that the addition of the fluid in step (iv) does not cause significant disruption to the shape of the droplet.

The cooled droplets formed in step (iii) may, for example, be frozen or be in the form of a gel. A gel is defined herein as a substance which under the conditions of the present method acts as a solid (i.e. deforms elastically and recovers and does not flow as a liquid would flow). It is preferred that the cooled droplets formed in step (iii) are frozen.

The cooled droplets formed in step (iii) may, for example, be in the form of a liquid. Such a liquid would typically be of a sufficiently high viscosity that the fluid added in step (iv) does not cause a substantial change in the shape of the particle i.e. the shape of the solid beads is substantially the same as that of the cooled droplets.

The solid beads formed in step (iv) typically have approximately the same shape as the cooled droplets from which the solid beads are derived. For example, the cooled droplets may be substantially spherical in shape, in which case the solid beads are typically substantially spherical in shape.

Step (iv) may take place in a conduit of the microfluidic device. The functional fluid may comprise a target material which is desired to be entrapped within the solid beads. The target material may be a material which, in step (ii), is dissolved or suspended within the solvent.

The fluid added in step (iv) is selected, having regard to the identity of the target material (typically a polymer) and the functional fluid solvent, to be an anti-solvent. Typically the fluid is a liquid in which the solvent is soluble and in which the solute (typically the polymer) has a low solubility (for example, is substantially insoluble). It is possible, instead, for the fluid to be in gaseous form, for example the fluid may comprise an anti-solvent vapour in admixture with an inert gas such as nitrogen. Whilst not wishing to be bound by theory, it is understood that addition of said fluid causes the solvent in the cooled droplet to dissolve in the liquid, leaving a solid segment comprising a "matrix" of polymer. If the polymer is soluble in said liquid, the developing beads would collapse.

Thus, it is believed that, in practice, the polymer typically precipitates, on substantially full desolvation of the droplet, to form a substantially spherical matrix of solid polymer, incorporating the target material, that is, especially one or more pharmaceutical agents. It is also possible, by appropriate selection of solvents, to obtain solid beads in the form of a gel.

The shape and size of the solid beads will depend on the method used to make said beads (and will depend to a large degree on the size of the conduits, the flow rates of the various fluids and the junction geometry). The beads made by the method of the present invention are typically substantially spherical and may have a mean diameter of from about 0.01 mm to about 2 mm. The size of the beads may depend on the intended use of the beads. For example, the solid beads may have a mean diameter of from about 0.01 to 0.5 mm. Beads of this size may typically be for pharmaceutical use. The beads may have a mean diameter of from 0.5 mm to 2 mm. Beads of this size may typically be used in assays.

Those skilled in the art will realise that the solid beads need not be totally free of solvent.

The solute typically comprises a polymer, such as a biocompatible polymer. Biocompatible polymers enable the solid beads to be administered to a patient for the delivery of a pharmaceutically active agent (if present) to the patient. Examples of polymers which may be used in the present invention are polylactides, polyglycolides, polycaprolactones, polyanhydrides and copolymers of lactic acid and glycolic acid. Further examples of suitable polymers are given in US2007/0196416 (see, in particular, paragraph [0013]). It will be appreciated that, where the beads are for pharmaceutical use, the polymer will preferably be one that is degradable in vivo. If the beads are intended for use a part of an assay, then it may be preferred for the polymer to be soluble in water, preferably water at a temperature which is not detrimental to any of the contents of the bead (an antibody, for example), such temperature typically being from 25 to 37° C.

The solvent may be a water-miscible organic solvent, and may typically be a polar aprotic solvent. Selection of a suitable solvent having regard to the polymer being used for use in a method according to the invention will be a matter of routine for those skilled in the art. Illustrative of solvents that may be used are, for example, DMSO, triacetin, glycofurol, PEG2000, N-methyl pyrrolidone, and hexafluoroisopropanol.

In or as the fluid added in step (iv) there may be used any fluid that is an anti-solvent for the polymer. Suitable anti-solvents may include, for example, water, methanol, ethanol, propanol, butanol, pentanol, hexanol, heptanol, octanol and higher alcohols; diethyl ether, methyl tert butyl ether, dimethyl ether, dibutyl ether, simple hydrocarbons, including pentane, hexane, heptane, octane and higher hydrocarbons. If desired, a mixture of solvents may be used. Other solvents, including suitable water-immiscible solvents, may be used.

It will be appreciated that the selection of functional fluid solvent and of anti-solvent will need to take into account the conditions, including in particular the temperature, to which they will be subjected during the method of the invention.

In certain circumstances, it may be preferred that the solvent is water. In this case, the anti-solvent may comprise a water-miscible organic solvent.

The functional fluid may further comprise a target material to be encapsulated in the solid bead. The target material may be incorporated in the functional fluid as a particulate or may be dissolved. Examples of particulates include colloids (such as gold colloids). The target material may comprise one or more component for use in an assay. The target material may comprise a pharmaceutically active agent, or may be a precursor of a pharmaceutically active agent. The pharmaceutically active agent may be, for example, any agent that is suitable for parenteral delivery, including, without limitation, fertility drugs, hormone therapeuticals, protein therapeuticals, anti-infectives, antibiotics, antifungals, cancer drugs, pain-killers, vaccines, CNS drugs, and immunosupressants. The delivery of drugs in polymer beads, especially by controlled release parenteral delivery, has particular advantages in the case of drugs which, for example, have poor water-solubility, high toxicity, poor absorption characteristics, although the invention is not limited to use with such agents. The active agent may be, for example, a small molecular drug, or a more complex molecule such as a polymeric molecule. In one advantageous embodiment, the pharmaceutically active agent may comprise a peptide agent. The term "peptide agent" includes poly(amino acids), often referred to generally as "peptides", "oligopeptides", "polypeptides" and "proteins". The term also includes peptide agent analogues, derivatives, acylated derivatives, glycosylated derivatives, pegylated derivatives, fusion proteins and the like. Peptide agents which may be used in the method of the present invention include (but are not limited to) enzymes, cytokines, antibodies, vaccines, growth hormones and growth factors. Further examples of suitable peptide agents are given in US2007/0196416 (see, in particular, paragraphs [0034] to [0040]). In a preferred embodiment, the pharmaceutically active agent is a gonadotropin releasing hormone agonist (GnHR). For example, the GnRH agonist may be leuprolide or a precursor thereof. Advantageously, the GnRH agonist-containing beads are provided in an administration form for locally targeted delivery, for example, in an implant.

The functional fluid may comprise a solute comprising one or more saccharide moieties. The solute may comprise a monosaccharide, a disaccharide, an oligosaccharide or a polysaccharide. The solute may comprise a saccharide derivative, such as a glycolipid, a glycoprotein, a glucoside, an amine or an acid. The solute may comprise a saccharide analogue or mimetic (such as those described in "Oligosaccharide mimetics", Glyoscience, H. P. Wessel and S. D. Lucas, 2079-2112, 2008). For example, an interglycosidic O atom may be replaced with another group, such as a spacer group. The functional fluid may comprise sufficient saccharide solute such that, in step (iv), a solid particle of solute is formed.

The functional fluid may comprise a solute comprising a polyol (a compound comprising two or more hydroxyl groups). Examples of such polyols are sugar alcohols, such as glycol, mannitol, lactitol and sorbitol. Those skilled in the art will realize that saccharide compounds may be polyols (to the extent that they comprise two or more hydroxyl groups), but not all polyols comprise saccharide moieties.

The functional fluid may comprise a solute comprising a polyol and a solute comprising a saccharide moiety (such as those compounds described above).

It is anticipated that the use of water-soluble saccharide and/or polyol compounds will facilitate the encapsulation and release of reagents such as enzymes without significantly affecting their tertiary structure.

The functional fluid may comprise an aqueous solution.

The target material may comprise one or more of an unlabelled oligonucleotide, a labelled oligonucleotide, labelled deoxynucleoside triphosphates, unlabelled deoxynucleoside triphosphates, labelled oxynucleoside triphosphates, unlabelled oxynucleoside triphosphates, enzyme for the amplification and/or synthesis of polynucleotides, magnesium ions, potassium ions, sodium ions, a polynucleotide, a stain or dye and a compound that, in use, produces a buffering effect. Such reagents are useful in amplification reactions (such as polymerase chain reactions [PCR]).

The target material may comprise one or more, of an antibody, an antigen, a label, a detergent and a solid phase. Such reagents and components are useful in performing assays.

The target material may comprise a positive internal control. A positive internal control typically comprises something which will produce a positive result if the assay is working properly. For example, the internal positive control may be in the form of exogenous DNA, if the assay is an amplification assay (such as a polymerase chain reaction [PCR] assay).

The target material may comprise an enzyme, functional protein, particles, RNA and nanoparticles (particles having a largest dimension of less than 1000 nm).

The carrier fluid will typically be an inert liquid that will remain liquid under the temperatures to be encountered during the process and that is immiscible with the functional fluid solvent. The carrier fluid may be immiscible with the fluid to be added in step (iv). Illustrative examples of carrier fluids that may be usable include various viscosity silicone oils, mineral oil, triglycerides, and squalene.

It is preferred that the device comprises a cooling conduit arranged for receiving the segmented flow from the junction region. It is further preferred that the device is provided with a cooler operable to cool fluid in the cooling conduit.

The device may comprise a desolvating conduit arranged for receiving fluid from the cooling conduit.

The device may comprise an anti-solvent inlet for introducing an anti-solvent into the desolvating conduit.

The conduits mentioned above need not be discretely-identifiable conduits. For example, the cooling conduit and carrier fluid conduit may be merged into one another.

The cooler may comprise a body comprising a thermally conductive material (such as a metal, for example, 316 stainless steel or aluminium). The body is typically cooled when the cooler is operated. The cooling of the body may be used to cool the cooling conduit. The body may be provided with a chilling channel for the carriage of a chilling fluid. The passage of a chilling fluid (typically a cold liquid) through the chilling channel causes the body to cool. The chilling fluid preferably has a melting point of lower than −50° C. The chilling fluid is typically cooled externally of the device, for example, by a refrigeration device.

The body of the cooler may further be provided with a heater. Such a heater may be used to heat the body; this may be useful in thawing any frozen liquids which may block any of the conduits of the device.

The device may be provided with a second thermally conductive body, the second thermally conductive body being associated with the carrier fluid conduit and the functional fluid conduit. The second thermally conductive body may be provided with a heater and/or cooler operable to regulate the temperature of liquids in the carrier fluid conduit and functional fluid conduit.

A thermally insulating gap may be provided between the body of the cooler and the second thermally conductive body. The thermally insulating gap may comprise a thermally insulating material, such as air. The gap helps inhibit cooling of the carrier fluid conduit and functional fluid conduit when the cooler is used to cool the cooling conduit.

The second thermally conductive body may be provided with a carrier fluid inlet for providing fluid to the carrier fluid conduit. The second thermally conductive body may be provided with a functional fluid inlet for providing fluid to the functional fluid conduit.

It is preferred that the device comprises one or more anti-solvent delivery conduits for delivering anti-solvent to the desolvating conduit via the anti-solvent inlet.

It is preferred that the cooling conduit arranged for receiving the segmented flow from the junction region is provided in a substrate (for example, by removing material from a substrate by milling or by laser action).

It is preferred that one or more of the carrier fluid conduit, the functional fluid conduit, the desolvating conduit and the anti-solvent conduit(s) are provided in a substrate.

It is further preferred that the substrate is in thermal contact with the cooler. If the cooler comprises a body of thermally conductive material, it is preferred that the substrate is in intimate contact with the body of thermally conductive material.

If the cooler comprises a body of conductive material, the body may be provided with one or more fluid inlets for delivering fluid to the anti-solvent delivery conduit (if present).

The term "microfluidic" is generally well-understood by those skilled in the art. The conduits in such microfluidic devices typically have widths of less than 2 mm, preferably less than 1 mm and more preferably from 0.1 to 0.5 mm. The depths of the conduits are typically less than 2 mm, preferably less than 1 mm and more preferably from 0.1 mm to 0.5 mm.

The flow rates of the fluids through the various conduits will depend, inter alia, on the cross-sectional area of the conduits. The flow rate, for example, of the functional fluid through the functional fluid conduit may typically be from about 0.05 to 0.2 ml/hour (if the conduit has a cross-section of about 0.05 mm×0.15 mm). The flow rate, for example, of the functional fluid through the functional fluid conduit may typically be from about 1 to 20 ml/hour, (if the conduit has a cross-section of about 2 mm×2 mm). Such flow rates may be used when wanting to make larger particles, such as those which may be used in assays. The flow rate of the carrier fluid may typically be from about 2 to 3 ml/hour (if the conduit has a cross-section of about 0.3 mm×0.3 mm). The flow rate of the carrier fluid may typically be from about 5 to 30 ml/hour (if the conduit has a cross-section of about 2 mm×2 mm). Such flow rates may be used when wanting to make larger particles, such as those which may be used in assays. The flow rate of the anti-solvent may typically be from about 0.5 to 2 ml/hour (if the conduit has a cross-section of about 0.3 mm×0.3 mm). The flow rate of the anti-solvent may typically be from about 10 to 20 ml/hour (if the conduit has a cross-section of between 1 mm×1 mm and 2 mm×2 mm). Such flow rates may be used when wanting to make larger particles, such as those which may be used in assays.

It is preferred that the desolvating conduit has a larger cross-section than the cooling conduit. This may be achieved by providing an enlargement in the desolvating conduit. A relatively large volume desolvating conduit causes the speed of flow of particles through the desolvating conduit to be slower than that through the cooling conduit. This may be beneficial if the anti-solvent chosen works relatively slowly which may be desirable to retain beads of more uniform size.

The microfluidic device may preferably be a device in accordance with the first aspect of the present invention.

The geometry of the junction may be one of many different geometries known to those skilled in the art. For example, EP1358931 discloses a Y-shaped junction and WO0164332 discloses a T-shaped junction.

In certain circumstances, it has been found that the anti-solvent should not act too quickly. If the anti-solvent is a strong anti-solvent, the particle morphology of the beads may be adversely affected and/or the porosity may be undesirably high.

It is been found that certain anti-solvents lead to better entrapment of the target material in the solid segment. In order to achieve this, the anti-solvent should not be a good solvent for the target material. In this way, the addition of the anti-solvent does not cause significant removal of the target material from the segments. For example, using leuprolide acetate as active agent, a lactide/glycolide polymer as the bead polymer, and various C3 to C8 alcohols as anti-solvent, retention of from about 60 to 95% of the active has been achieved.

In accordance with a third aspect of the present invention, there is provided a plurality of beads made in accordance with the method of the second aspect of the present invention.

In accordance with a fourth aspect of the present invention, there is provided a plurality of beads having a mean largest dimension of from about 0.01 mm to 0.5 mm (preferably from about 0.01 mm to 0.2 mm) and a standard deviation of the maximum dimension of less than 5% (preferably less than 3%) of the mean largest dimension, the beads comprising a biocompatible polymer and a pharmaceutically active agent, (or precursor thereof).

In accordance with a fifth aspect of the present invention, there is provided a plurality of beads having a mean largest dimension of from about 0.5 mm to 2 mm (preferably from about 0.8 mm to 1.5 mm) and a standard deviation of the maximum dimension of less than 5% (preferably less than 3%) of the mean largest dimension, the beads comprising one or more components for use in an assay. It is preferred that the beads are readily soluble in water at 25-37° C. It is further preferred that the beads comprise a water-soluble saccharide and/or polyol compound. It is further preferred that the beads comprise a matrix or supporting structure of water-soluble saccharide and/or polyol compound. It is further preferred that the beads comprise one or more of an antibody, an antigen, one or more particles, a label, a detergent and a solid phase. Such beads may be of use in assays.

In accordance with a sixth aspect of the present invention, there is provided a method of performing an assay comprising providing a plurality of beads in accordance with the third or fifth aspects of the present invention. The method may comprise other steps, such as placing the plurality of beads in intimate admixture with a liquid suitable for releasing material incorporated in the beads. Such material may be the target material referred to in the first to fifth aspects of the present invention. Release of material from the beads may occur, for example, by dissolving or partially dissolving the beads. Alternatively, the liquid may swell the beads.

The invention will now be described by way of example only with reference to the following figures of which:

FIG. 1 is a plan view of an example of an embodiment of a microfluidic device in accordance with the present invention;

FIG. 2 is a plan view of the underlying cooling body used in the device of FIG. 1;

FIG. 3 is a cross-sectional view along AA of the device of FIG. 1;

FIG. 4 is a schematic cross-sectional view along AA of the substrate of the device of FIG. 1 showing in more detail the relative arrangements of the conduits;

FIG. 5 is a plan view of a further cooling body;

FIG. 6 is a schematic view of desolvation of a droplet in a method of the invention;

FIG. 7 is a graph illustrating cooling in the device of the invention;

FIG. 8 is a graph illustrating the heating-cooling characteristics of different parts of a device according to one embodiment of the invention;

FIG. 9 is a plan view of a further example of an embodiment of a microfluidic device in accordance with the present invention;

FIG. 10 is a plan view of the underlying cooling body used in the device of FIG. 9; and FIG. 11 shows that an antibody retains its activity when incorporated into solid beads using the device of FIGS. 9 and 10.

An example of an embodiment of a device of the present invention will now be described with reference to FIGS. 1 to 4. The device is denoted generally by reference numeral 300 and comprises a substrate 200 placed in intimate contact with a cooling body 100. The substrate is, of polytetrafluoroethylene and has formed within it a carrier fluid conduit 201 for the carriage of a carrier fluid and a functional fluid conduit 202 for the carriage of functional fluid. The carrier fluid conduit 201 is approximately 0.3 mm wide and 0.3 mm deep. At the point at which the functional fluid conduit 202 meets the carrier fluid conduit 201, the functional fluid conduit 202 has an approximately circular cross-section, with a diameter of about 50 to 150 μm. The carrier fluid conduit 201 and the functional fluid conduit 202 meet at a junction region 210 (best seen in FIGS. 3 and 4). In use, droplets of functional fluid within a flow of carrier fluid are formed immediately downstream of the junction. A cooling conduit 203 extends downstream from the junction region 210. The cooling conduit is about 0.3 mm deep and 0.3 mm wide. In use, a segmented flow of droplets of functional fluid carried in the carrier fluid passes from the junction region 210 to the cooling conduit which is cooled by the cooler body 100 as described below to form cooled (typically solid) droplets. The droplets may, for example, be frozen or may be in the form of a gel.

A desolvating conduit 205 extends downstream from the cooling conduit to the device outlet 206, so that, in use, the segmented flow of carrier fluid and cooled droplets passes into the desolvating conduit. Two anti-solvent conduits 207, 208 (each about 0.3 mm deep and 0.3 mm wide) converge with the desolvating conduit so as to be able to deliver anti-solvent to the desolvating conduit. This anti-solvent causes solvent (but not the polymer solute) to leave the cooled droplet, thus forming solid beads. Desolvation is illustrated schematically in FIG. 6, in which an advancing flow of carrier fluid carrying a substantially spherical droplet of functional fluid (a) passes from an upstream portion of cooling conduit 203 into desolvating conduit portion 205, past converging anti-solvent conduits 207, 208. Anti-solvent entering through conduits 207, 208 forms a laminar flow in which the segmented flow is enclosed by the anti-solvent flow. The cooled droplets (b) contact the interface between carrier fluid and anti-solvent. Because at least one component of the droplet has an affinity for (preferably is soluble in) the anti-solvent, there is a tendency for the cooled droplet (c) to pass into the anti-solvent flow. As a result of the contact between cooled droplet and antisolvent, desolvation takes place and the polymer is precipitated. Because desolvation, in the method of the invention, takes place at a rate somewhat limited by the conditions under which desolvation takes place, the precipitation of the polymer can typically occur such that a matrix with a desirable morphology, narrow particle size range and desirable porosity is obtained. Beads with a relatively uniform morphology having a particle size within a relatively narrow range offer the advantage that, when used in drug delivery, they can provide improved drug release characteristics as compared with beads having less uniform morphology and particle size. Size and size distribution of beads can affect a number of characteristics of drug delivery, including the rate of release, the effectiveness of targeting, suspension properties in a dispersion, and the syringability. Thus, the relatively narrow size distribution of the particles obtainable in accordance with the invention can, in a variety of therapeutic products, favourably influence one or more of those characteristics. Administration forms in which the beads of the invention may be used include any in which the delivery of a therapeutic agent in porous beads (also referred to as microspheres) may be suitable. Such administration forms may be for drugs for systemic use or for locally targeted delivery and in particular, but not exclusively, include injectable formulations and implants.

In the method of the present invention, the solvent is generally soluble in (and miscible with) the anti-solvent. The polymer solute is soluble in the solvent, but insoluble in the anti-solvent.

The desolvating conduit comprises an enlargement or widening 209. Downstream of the enlargement the desolvating conduit has a depth and width of approximately 0.5 mm.

Carrier fluid is transferred to the carrier fluid conduit through a carrier fluid inlet 103 formed in a thermally conductive body 113. Functional fluid is transferred to the functional fluid conduit through a functional fluid inlet 102 formed in the thermally conductive body 113. Anti-solvent is transferred to the anti-solvent conduits 207, 208 through two anti-solvent inlets 106, 107 formed in the cooler body 100. This arrangement of inlet passages being formed through the cooler body 100 and the thermally conductive body 113 facilitates the simple introduction of fluids to the substrate 200.

The cooler body 100 is provided with a chilling channel 101 for the passage therethrough of chilling liquid. The chilling liquid used in the present example is silicone oil. The oil is cooled externally of the device and pumped into the chilling channel 101. The passage of chilling liquid through the chilling channel causes the cooler body to become cold. Furthermore, the chilling liquid causes the region of cooler body adjacent to the chilling liquid conduit to become especially cold. In use, this region of the cooler body is adjacent to the portion of the substrate 200 provided with the cooling conduit 203, thus causing any droplets of functional fluid present in the cooling conduit 203 to freeze.

An insulating gap 109 is provided between the cooler body 100 and the body of thermally conductive material 113. The gap comprises insulating material (such as air).

The choice of the temperature of the chilling fluid should be selected to produce sufficiently cooled droplets of the functional fluid whilst the carrier fluid remains liquid. For example, the choice of the temperature of the chilling fluid may be selected to produce frozen droplets of the functional fluid.

The anti-solvent may be chilled, too ("chilled" meaning being at a temperature less than ambient temperature).

The conduits in the substrate 200 are produced by removing material by micromilling using a Roland EGX-300 engraver or by laser drilling. The smaller conduits (typically those having a diameter of 50-100 microns) are in the form of apertures which may be produced using, for example, laser drilling.

Those skilled in the art will realise that the size of beads, produced by the device and method of the present invention depends on the flow rates of the carrier and functional fluids and the sizes of the carrier fluid conduit and the functional fluid conduit.

The surfaces in contact with the fluids should be of a low energy and are typically formed by machining a substrate of low energy material (e.g. polytetrafluoroethylene [PTFE, for example, Teflon®]) or by machining a high energy substrate and coating with a low energy material (e.g. by vapour deposition).

Those skilled in the art will realise that alternative coolers may be used. For example, Peltier coolers could be used. Peltier coolers are widely available, for example, from UWE Electronic GmbH, Unterhaching, Germany.

Those skilled in the art will realise that the junction arrangement used above may be replaced by different junction arrangements known to those skilled in the art. For example, EP1358931 discloses a Y-shaped junction and WO0164332 discloses a T-shaped junction.

Figure 5:
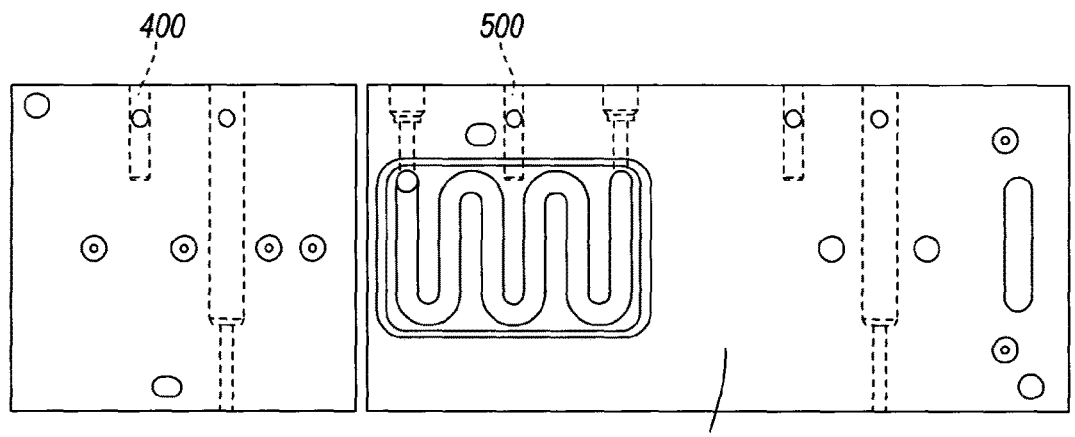
Figure 6:
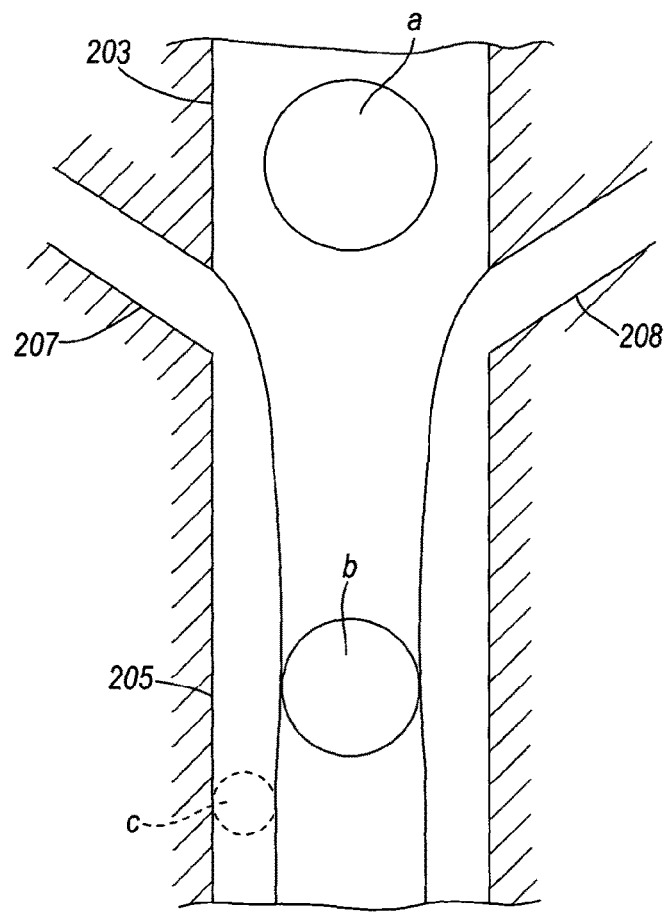

A cooling body 100' of a device similar to that of FIGS. 1 to 4 is shown in FIG. 5. The cooler body is similarly constructed in most respects to the cooler body of FIGS. 1 to 4. In the cooler body of FIG. 5, however, there are additionally provided a thermocouple 400 for measuring temperature of the cooler in the region of the carrier fluid conduit and the functional fluid conduit and a thermocouple 500 for measuring the temperature of the cooler body in the region of the cooling conduit.

In the example of the embodiment of the device, the polymer and active agent are mixed together and introduced via one conduit into the device. It is possible to introduce the active agent via a different conduit to the polymer, for example, by providing an active fluid conduit which meets the functional fluid conduit upstream of the junction between the functional fluid conduit and the carrier fluid conduit. Mixing within a droplet may be achieved using velocity profile mixing as induced by segmented flow.

The desolvating conduit is shown in the present example as being straight. The desolvating conduit may be convoluted (for example, by being curved e.g. a spiral) to ensure that the anti-solvent effect occurs over a long time scale.

Figure 2:
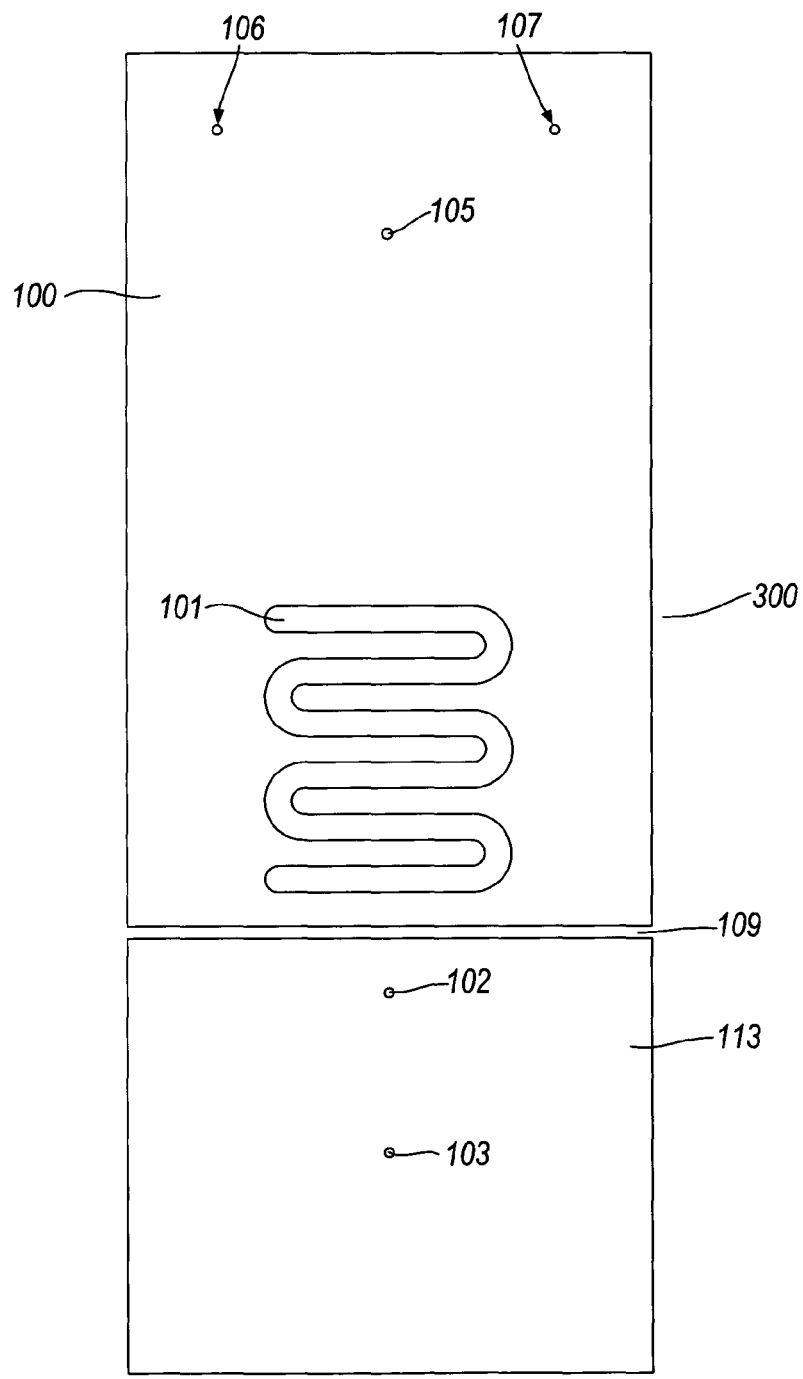

The use of the device of FIGS. 1 to 3 in several examples of embodiments of a method in accordance with the present invention will now be described.

General Method

Carrier fluid (silicone oil) is introduced, using a pump, into the carrier fluid conduit 201 via carrier fluid inlet 103. The carrier fluid, for example, a 100 cst silicone oil (that is, a silicone oil having viscosity 100 mPa·s at 20° C.) passes through carrier fluid conduit 201, through the cooling conduit 203 and out of the outlet 206 via the desolvating conduit 205. Carrier fluid is permitted to flow through the device for a short period of time. Chilling fluid is then fed through the chilling conduit 101 of cooler body 100. Anti-solvent (for example, an organic alcohol, such as pentanol) is then introduced into the anti-solvent conduits 207, 208 via anti-solvent inlets 106, 107. The anti-solvent enters the desolvating conduit and moves to the exit.

Once the cooler body has reached the desired temperature, the functional fluid is introduced into the functional fluid conduit 202 via functional fluid inlet 102. The functional fluid may, for example, comprise a solution of a biocompatible polymer and a pharmaceutically active material. The flow rates of the functional fluid and carrier fluid are such that there is formed a segmented flow of functional fluid droplets in carrier fluid immediately downstream of the junction region 210. Typically, the flow rates of the carrier fluid and functional fluid are 1-4 ml/hour (often 2.5 ml/hour) and 10-200 microl/hour (often 50 microl/hour), respectively. Both the carrier fluid and functional fluid are stabilised at a predetermined temperature (for example, at 20° C.) before being introduced into the device.

The droplets of functional fluid are sufficiently chilled in the cooling conduit 203 that the solvent used in the functional fluid is sufficiently cooled (preferably solidified [for example, frozen, or formed into a gel]). The droplets are typically sufficiently cooled within the first 20-30 mm length of the cooling conduit (this being especially the case if the droplets are frozen, as opposed to formed into a gel). The chilling liquid passing through the chilling channel 101 is at −25° C. The segmented flow of cooled droplets in carrier fluid is then transferred to the desolvating conduit 205. The anti-solvent causes the solvent to leave the cooled droplets, thus forming generally solid beads, which leave the device via outlet 206. The flow rate of anti-solvent is typically 1-4 ml/hour (0.5-2 ml/hour through each of the anti-solvent conduits 207, 208), with 0.8-1 ml/hour being an often-used flow rate.

Figure 7:
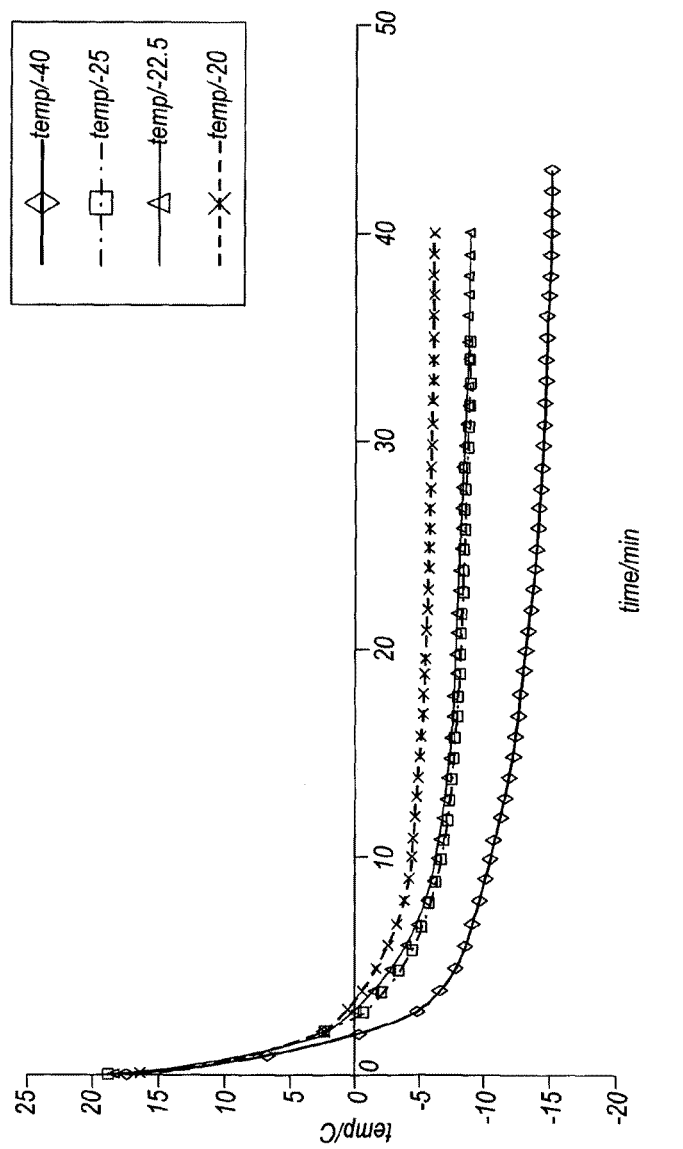

The temperature of the chilling fluid in the chilling conduit 101 is variable. The temperature in the cooler body 100 in the region of the cooling conduit can be monitored, for example by the thermocouple 500 as shown in FIG. 5. Four illustrative cooling curves for the cooling body are shown in FIG. 7 in which the device is cooled from ambient using chilling fluid at −40° C., −25° C., −22.5° C. or −20° C. The temperature of the cooling body is measured by the thermocouple 500 and reduces according to the respective cooling curve in FIG. 7.

The device of the invention allows independent control of temperature in the cooling conduit and upstream areas of the device respectively, as illustrated with reference to FIG. 8.

Figure 8:
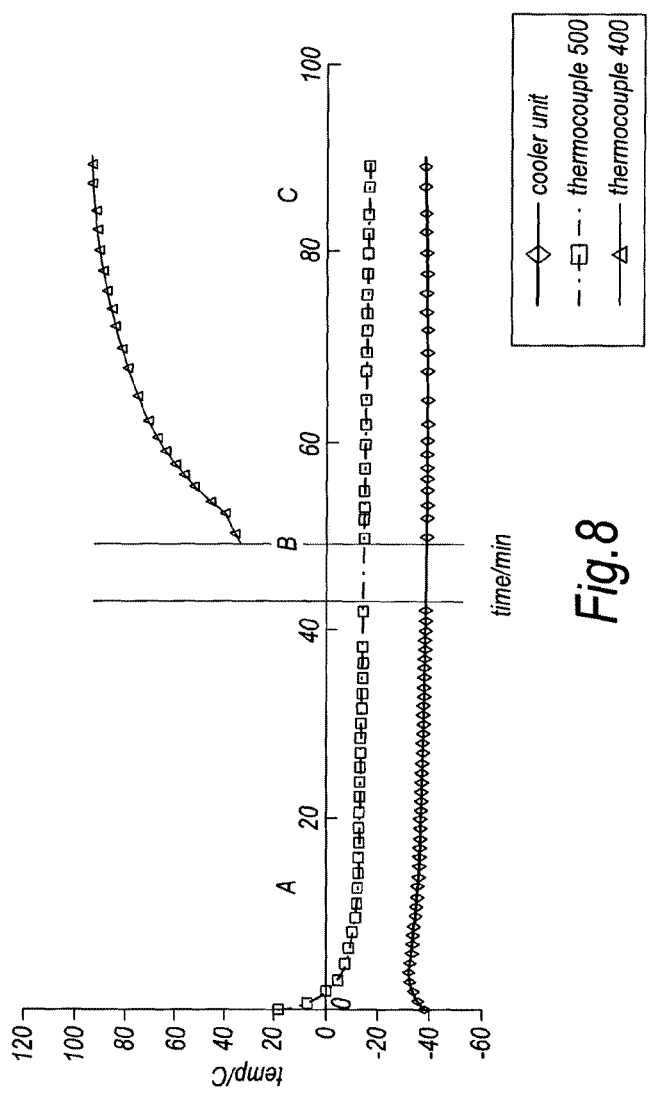

Illustrative temperature measurements are shown in FIG. 8 for thermocouples 400 and 500, during a heating/cooling regime as described below.

Cooler unit initial temperature −40° C.
Manifold initial temperature 17.9° C.
Final manifold temperature −15.3° C.
Thermocouple 400 initial temperature=37° C.
Thermocouple 400 final temperature=95° C.

Zone A: Cooling curve—Started the cooling unit first and recorded the temperatures of the manifold and cooler unit at the same time. The temperature of the cooler unit fluctuated at the beginning and stabilized after 17 minutes. The temperature of the manifold sharply decreased over the first 5 minutes then gradually reduced to a temperature of −15.3° C.

Zone B: After cooling, the manifold was heated on the left hand side. The temperature of the manifold began to increase after 7 minutes.

Zone C: Cooling-heating interaction curve. The temperature of the manifold started to increase 7 min (Zone B) after introducing heat and became stable after 47 minutes. The temperature of the manifold (right hand side) increased by +3° C. in total from start to finish.

The above regime shows that the temperature of the upstream part of the device can be heated independently, and with effective thermal insulation from, the cooling region.

The solute (the polymer) should not be significantly soluble in the anti-solvent otherwise segments may collapse on addition of the anti-solvent.

As already stated, the particles are typically substantially spherical in shape. The mean diameter may be ascertained by any suitable method. For example, the mean diameter of the particles may be ascertained by viewing a multiplicity of particles under an electron microscope, measuring the diameter of a representative sample of, for example, 15 particles, and ascertaining the mean diameter therefrom.

The Following Examples Illustrate the Invention

EXAMPLE 1

The general methodology described above was used. The functional fluid introduced into the functional fluid conduit comprised a copolymer of lactide and glycolide (PLGA) dissolved in dimethyl sulfoxide (DMSO). The concentration of the solution was 10% w/v. The copolymer comprised 75% lactide units and 25% glycolide units, and had a $M_w$ of 66,000-107,000, available from Sigma Aldrich as P1941 Poly(DL-lactide-co-glycolide).

The flow rates in the device were as follows:
Functional fluid flow rate: 0.05 mL/h
Carrier fluid flow rate: 3 mL/h
Anti-solvent fluid flow rate: 0.5 mL/h
The anti-solvent flow rate indicated above relates to each of two anti-solvent conduits; thus the combined anti-solvent flow rate taking account of both anti-solvent feed was 1 mL/h.

On entering the cooling part of the device, the functional fluid formed frozen droplets. Desolvation of the frozen droplets caused the formation of solid beads. The carrier fluid comprised 100 cst silicone oil. The anti-solvent comprised ethanol The beads so produced were spherical in shape. The size of the spheres was measured using scanning electron and light microscopy. Three batches of solid segments were made using the same functional fluid. The size of 15 segments was measured for each batch, yielding the mean diameters with standard deviation values (S.D.) listed below:
Batch 1—115.1 μm, S.D.=2.0 μm
Batch 2—121.4 μm, S.D.=1.8 μm
Batch 3—108.9 μm, S.D.=1.8 μm

EXAMPLE 2

The general methodology described above was used. The functional fluid introduced into the functional fluid conduit comprised a copolymer of lactide and glycolide (PLGA) dissolved in dimethyl sulfoxide (DMSO). The concentration of the solution was 10% w/v. The copolymer comprised 65% lactide units and 35% glycolide units, and had a $M_w$ of 40,000-75,000, available from Sigma Aldrich as P2066 Poly(DL-lactide-co-glycolide)).

The flow rates were as used in Example 1.

On entering the cooling part of the device, the functional fluid formed frozen droplets. Desolvation of the frozen droplets caused the formation of solid beads. The carrier fluid comprised 100 cst silicone oil. The anti-solvent comprised ethanol. Three batches made using the same conditions.

The beads so produced were spherical in shape. The size of the spheres was measured using scanning electron and light microscopy. Three batches of solid segments were made using the same functional fluid. The size of 15 segments was measured for each batch, yielding the mean diameters listed below:

Batch 1—97.0 μm, S.D.=2.4 μm
Batch 2—101.8 μm, S.D.=2.0 μm
Batch 3—99.2 μm, S.D.=1.7 μm

EXAMPLE 3

The general methodology described above was used. The functional fluid introduced into the functional fluid conduit comprised a copolymer of lactide and glycolide (PLGA) dissolved in dimethyl sulfoxide (DMSO). The concentration of the solution was 10% w/v. The copolymer comprised 50% lactide units and 50% glycolide units, and had a $M_w$ of 40,000-75,000, available from Sigma Aldrich as P2191 Poly(DL-lactide-co-glycolide)).

The flow rates were as used in Example 1.

The carrier fluid comprised 100 cst silicone oil. The anti-solvent comprised ethanol.

On entering the cooling part of the device, the functional fluid formed frozen droplets. Desolvation of the frozen droplets caused the formation of solid beads. The beads so produced were spherical in shape. The size of the spheres was measured using scanning electron microscopy. Three batches of solid segments were made using the same functional fluid. The size of 15 segments was measured for each batch, yielding the mean diameters listed below:

Batch 1—95.6 μm, S.D.=1.3 μm
Batch 2—97.1 μm, S.D.=1.8 μm
Batch 3—98.1 μm, S.D.=1.7 μm In Examples 1, 2 and 3, no so-called "active" ingredient was included in the functional fluid. It has been found that the incorporation of certain "active" ingredients (such as leuprolide acetate) into the functional fluid does not have an appreciable effect on the size of the segment produced.

In the Examples 1 to 3 the method of the invention enables there to be obtained polymer beads with a relatively consistent morphology and within a relatively narrow particle size range. That can offer particular advantages in drug delivery in terms of, for example, consistency and/or predictability of the release of a therapeutic substance contained within the beads.

EXAMPLE 4

The entrapment of pharmaceutically active compound was investigated to determine the effect of using different anti-solvents.

The general methodology described above was used. Leuprolide acetate dissolved in DMSO/PLGA mixture at between 1-5 mg/ml of solution. The 50:50 lactide/glycolide polymer P2191 used in Example 3 was used in this Example, at a concentration of 10% w/v.

The flow rates were as used in Example 1. On entering the cooling part of the device, the functional fluid formed frozen droplets. Desolvation of the frozen droplets caused the formation of solid beads.

Various anti-solvents were investigated to determine the effect of the anti-solvent on the amount of active agent (leuprolide acetate) retained in the beads. HPLC and/or NMR were used to determine the amount of leuprolide acetate retained.

| Anti-solvent | % active agent retained in solid beads |
|---|---|
| Ethanol and pentanol | 63 |
| Pentanol | 92 |
| Heptanol (batch 1) | 78 |
| Octanol:ethanol (80:20) | 76 |
| Octanol:ethanol (90:10) | 84 |
| Pentane | 94 |

These data demonstrate that the choice of anti-solvent is important. The anti-solvent should not be a good solvent for the polymer. Furthermore, the anti-solvent should not be a good solvent for the active ingredient.

Figure 9:
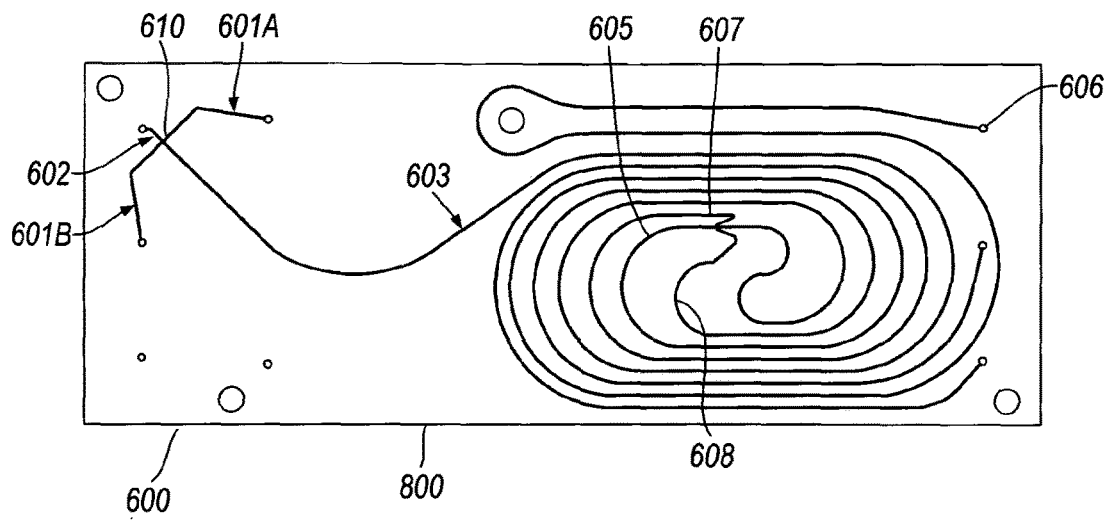
Figure 10:
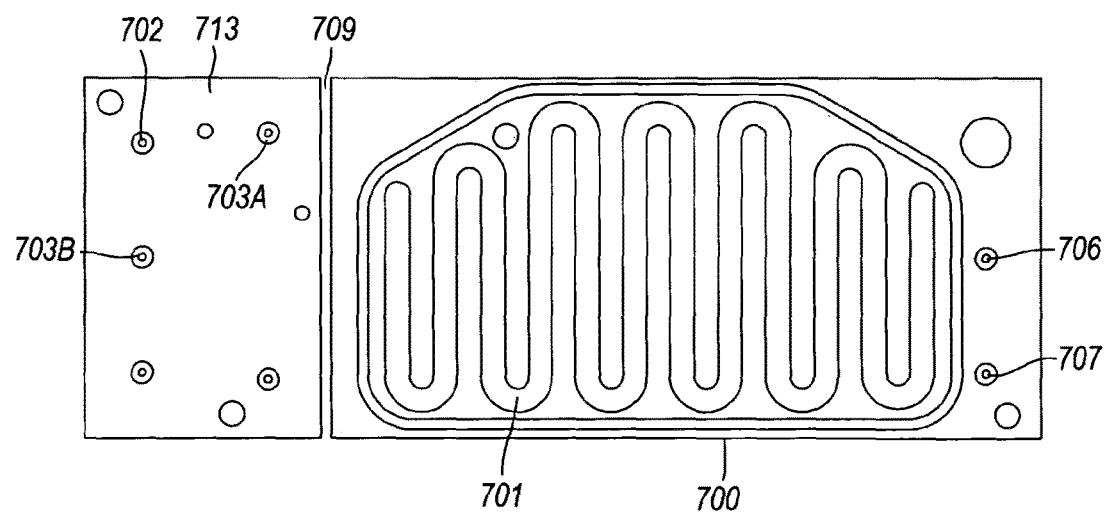

A further example of an embodiment of a device of the present invention will now be described with reference to FIGS. 9 and 10. The device is denoted generally by reference numeral 600 and comprises a substrate 800 placed in intimate contact with a cooling body 700. The substrate is of polytetrafluoroethylene and has formed within it two carrier fluid conduits 601A, 601B for the carriage of a carrier fluid and a functional fluid conduit 602 for the carriage of functional fluid. The carrier fluid conduits 601A, 601B and the functional fluid conduit 602 are each approximately square in cross-section and approximately 1 mm wide and 1 mm deep. The carrier fluid conduits 601A, 602B and the functional fluid conduit 602 meet at a junction region 610. In use, droplets of functional fluid within a flow of carrier fluid are formed immediately downstream of the junction. A cooling conduit 603 extends downstream from the junction region 610. The cooling conduit is about 1.4 mm deep and 1.4 mm wide. In use, a segmented flow of droplets of functional fluid carried in the carrier fluid passes from the junction region 610 to the cooling conduit which is cooled by the cooler body 700 to form solid droplets.

A desolvating conduit 605 (having an approximately square cross-section of width and depth of 1.7 mm) extends downstream from the cooling conduit to the device outlet 606, so that, in use, the segmented flow of carrier fluid and solid droplets passes into the desolvating conduit. Two anti-solvent conduits 607, 608 (each about 0.7 deep and 0.7 mm wide) converge with the desolvating conduit so as to be able to deliver anti-solvent to the desolvating conduit. This anti-solvent causes solvent (but not the polymer solute) to leave the solid droplet, thus forming solid beads.

Desolvation occurs generally as described above in relation to FIGS. 1 to 4.

Carrier fluid is transferred to the carrier fluid conduits through carrier fluid inlets 703A, 7038 formed in a thermally conductive body 713. Functional fluid is transferred to the functional fluid conduit through a functional fluid inlet 702 formed in the thermally conductive body 713. Anti-solvent is transferred to the anti-solvent conduits 607, 608 through two anti-solvent inlets 706, 707 formed in the cooler body 700. This arrangement of inlet passages being formed through the cooler body 700 and the thermally conductive body 713 facilitates the simple introduction of fluids to the substrate 800.

The cooler body 700 is provided with a chilling channel 701 for the passage therethrough of chilling liquid. The chilling liquid used in the present example is silicone oil. The oil is cooled externally of the device and pumped into the chilling channel 701. The passage of chilling liquid through the chilling channel causes the cooler body to become cold. Furthermore, the chilling liquid causes the region of cooler body adjacent to the chilling liquid conduit to become especially cold. In use, this region of the cooler body is adjacent to the portion of the substrate 800 provided with the cooling conduit 603, thus causing any droplets of functional fluid present in the cooling conduit 603 to solidify.

An insulating gap 709 is provided between the cooler body 700 and the body of thermally conductive material 713. The gap comprises insulating material (such as air).

EXAMPLE 5

The general methodology described above in relation to FIGS. 9 and 10 was used. The functional fluid introduced into the functional fluid conduit comprised a 12% w/v solution of poly(ethylene oxide) [181994 poly(ethylene oxide), Sigma Aldrich, UK, $M_w$-200,000] in a 55:45 mixture of dimethyl sulfoxide (DMSO) and water. The functional fluid was introduced into the functional fluid conduit using a heated syringe.

The carrier fluid comprised 100 cst silicone oil.
The anti-solvent comprised 2-propanol.
The flow rates in the device were as follows:
Functional fluid flow rate: 1 mL/h
Carrier fluid flow rate: 8 mL/h
Anti-solvent fluid flow rate: 8 mL/h
The anti-solvent flow rate indicated above relates to each of two anti-solvent conduits; thus the combined anti-solvent flow rate taking account of both anti-solvent feeds was 16 mL/h.
The carrier fluid flow rate indicated above relates to each of two carrier fluid conduits; thus the combined carrier fluid flow rate taking account of both carrier fluid feeds was 16 mL/h.

The droplets of the poly(ethylene oxide) solution cool on entering the cooling portion of the device. Given that the freezing temperature of the DMSO:water solvent is about −40° C., it is not expected that the droplets would be frozen, rather that the droplets either form a gel or are cooled to form a very viscous liquid. The anti-solvent causes desolvation of the cooled droplets, thus forming solid beads. Even in the event that the cooled droplets were liquid (as opposed to a gel), the droplets were of sufficiently high viscosity that the beads formed from the cooled droplets were of essentially the same shape as the cooled droplets i.e. addition of the anti-solvent did not cause the droplets to deform.

The solid beads were collected and suspended in 2-propanol to ensure that the beads were substantially free of solvent. The beads were removed from the suspension by filtration and then dried.

It is anticipated that the step of suspending the beads in bulk anti-solvent prior to drying is not necessary. In the present case, this step was performed to ensure that the beads were free of solvent.

The beads so produced were spherical in shape. The size of the spheres was measured using light microscopy. Two batches of solid beads were made. The size of 30 segments was measured for each batch, yielding the mean diameters with standard deviation values (S.D.) listed below:
Batch 1—903 µm, S.D.=12 µm
Batch 2—954 µm, S.D.=11 µm
This illustrates that the device and method of the present invention may be used to produce beads of a generally monodisperse nature.

EXAMPLE 6

The method of Example 5 was repeated, but with an antibody (anti-streptavidin, labelled with fluorescein isothiocyanate, [Abcam plc, Cambridge, UK]) incorporated into the functional fluid.

The solid beads were assayed with streptavidin-bound microtitre plates to demonstrate that the antibody held within the beads retains its activity. FIG. 11 shows the fluorescent signal generated by the beads compared to various other standards and controls. "Blank bead" refers to beads containing no antibody. The results labelled "50 pmol", "25 pmol", "12.5 pmol" and "6.25 pmol" refer to the respective concentrations of four control solutions of anti-streptavidin. "Blank liquid" refers to a solution containing no antibody.

It is apparent that the antibody held within the beads has retained its activity.

ILLUSTRATIVE EXAMPLE

Whilst this example does not fall within the scope of the present invention because the method does not use a microfluidic device to produce droplets, the example illustrates the possibility of using the method and device of the present invention to produce solid droplets comprising a saccharide solute. It is anticipated that such droplets may be of particular use in assays, since the saccharide would be readily soluble in water or aqueous solution.

Solutions of 10% w/v of mannitol and dextran in water were prepared. The solutions were then added dropwise to ethanol.

The dextran solution produced amorphous particles in ethanol. The amorphous particles readily dissolved in warm water. The mannitol solution produced a microcrystalline precipitate which dissolved in warm water.

It is anticipated that a solution comprising both mannitol and dextran may be beneficial in that dextran appears to be suitable for forming discrete particles and mannitol may well be a suitable bulking agent. Furthermore, the mannitol may give the beads a more manageable consistency.

Attempts were made to make solid beads from the polyol solutions using the apparatus of FIGS. 1-4. The solutions formed liquid droplets in a satisfactory manner, but these droplets did not freeze. It is thought that further cooling of the apparatus is required in order to freeze the droplets. This may be achieved, for example, by improving the cooling capability of the cooler.

A solution of 10% w/v of mannitol in dimethyl sulphoxide (DMSO) was prepared. This was found to freeze at about 10° C. It is therefore anticipated that droplets made from this solution would freeze using the apparatus of FIGS. 1 to 4, and that solvent may be extracted from the frozen droplets using an anti-solvent, such as ethanol.

As mentioned above, it is anticipated that the saccharide-based droplets may be used in assays. In this case, it is likely that it would be desirable for a bead to have a diameter or largest dimension of about 0.5 mm to 2 mm. In this case, it would be desirable to adapt the apparatus of FIGS. 1 to 4 by having deeper and wider conduits (typically 2 mm×2 mm). Furthermore, the flow rates used to produce larger beads would typically be greater than the flow rates discussed above in Examples 1 to 4. For example, the flow rate of the functional fluid through the functional fluid conduit may typically be from about 1 to 20 ml/hour. The flow rate of the carrier fluid may typically be from about 5 to 30 ml/hour.

Where, in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims.

The invention claimed is:

1. A method of making solid beads, said method comprising:
   (i) providing a microfluidic device comprising a carrier fluid conduit and a functional fluid conduit which meet at a junction region;
   (ii) providing a laminar flow of a functional fluid comprising a solvent and a solute along the functional fluid conduit and providing a laminar flow of a carrier fluid along the carrier fluid conduit so as to form droplets of functional fluid in a flow of carrier fluid;
   (iii) cooling the droplets of functional fluid in a conduit of the microfluidic device to form cooled droplets; and
   (iv) bringing a liquid into contact with the cooled droplets, said solvent being soluble in said liquid so that the solvent exits the cooled droplets, thereby forming solid beads.

2. A method according to claim 1, wherein the cooled droplets formed in step (iii) are liquid, frozen or in the form of a gel.

3. A method according to claim 1 wherein the functional fluid comprises a target material which is desired to be entrapped within the solid bead.

4. A method according to claim 1 wherein the solute comprises a polymer.

5. A method according to claim 1 wherein the solvent comprises a water-miscible organic solvent, and the liquid added in step (iv) is water or a water-soluble organic solvent.

6. A method according to claim 1 wherein the device comprises a cooling conduit arranged for receiving the segmented flow from the junction region, and the device is provided with a cooler operable to cool fluid in the cooling conduit.

7. A method according to claim 6 wherein the device comprises a desolvating conduit arranged for receiving fluid from the cooling conduit.

8. A method according to claim 6 wherein the cooler comprises a body comprising a thermally conductive material and the body is provided with a chilling channel for the carriage of a chilling fluid.

9. A method according to claim 1 wherein the device is provided with a second thermally conductive body, the second thermally conductive body being associated with the carrier fluid conduit and the functional fluid conduit, the second thermally conductive body being provided with a heater and/or cooler operable to regulate the temperature of liquids in the carrier fluid conduit and functional fluid conduit and a thermally insulating gap is provided between the body of the cooler and the second thermally conductive body.

10. A method according to claim 1 wherein the flow rate of the functional fluid through the functional fluid conduit is from about 0.01 to 0.2 ml/hour, and the flow rate of the carrier fluid through the carrier fluid conduit is from about 1 to 4 ml/hour.

11. A method according to claim 1, in which the functional fluid further comprises a pharmaceutically active agent, the pharmaceutically active agent being selected from fertility drugs, hormone therapeuticals, protein therapeuticals, anti-infectives, antibiotics, antifungals, cancer drugs, pain-killers, vaccines, CNS drugs, and immunosupressants.

12. A method of making solid beads containing a therapeutic agent, said method comprising:
   (i) providing a microfluidic device comprising a carrier fluid conduit and a functional fluid conduit which meet at a junction region;
   (ii) providing a flow of a functional fluid comprising a solvent, a matrix-forming solute and said therapeutic agent along the functional fluid conduit and providing a flow of a carrier fluid along the carrier fluid conduit so as to form at or downstream of said junction droplets of functional fluid in a flow of carrier fluid;
   (iii) cooling the droplets of functional fluid in a conduit of the microfluidic device to form cooled droplets; and
   (iv) bringing a liquid into contact with the cooled droplets, said solvent being soluble in said liquid so that the solvent exits the cooled droplets, thus forming solid beads containing the therapeutic agent; and
   (v) removing the solid beads.

13. A plurality of beads made in accordance with the method of claim 1.

14. A method according to claim 1 wherein step (iv) takes place in a conduit of the microfluidic device.

15. A method according to claim 1, wherein the solvent comprises water, and the liquid added in step (iv) is a water-soluble organic solvent.

16. A method according to claim 15 wherein the functional fluid comprises a solute comprising a polyol and/or a solute comprising a polyol and/or a solute comprising a saccharide moiety.

17. A method according to claim 15 wherein the flow rate of the functional fluid through the functional fluid conduit is from about 1 to 20 ml/hour and the flow rate of the carrier fluid through the carrier fluid conduit is from about 5 to 30 ml/hour.

18. The method according to claim 1 wherein the cooled droplets formed by the (iii) cooling the segments of functional fluid in a conduit of the microfluidic device have sufficient structural integrity such that no significant disruption to the shape of the cooled droplet is caused by the (iv) bringing of the liquid into contact with the cooled droplets so as to cause said solvent to exit said cooled droplets, thus forming the solid bead.

* * * * *